US009327043B2

(12) United States Patent
Olchovy et al.

(10) Patent No.: US 9,327,043 B2
(45) Date of Patent: *May 3, 2016

(54) DEVICE FOR DELIVERING A VOLATILE FLUID TO THE ATMOSPHERE

(71) Applicant: The Procter & Gamble Company, Cincinnati, OH (US)

(72) Inventors: Jason John Olchovy, West Chester, OH (US); Stefano Deflorian, Trento (IT); Livio Sordo Sicheri, Trento (IT); Walter Sordo, Trento (IT); Ian Roderick Jaye, Detroit, MI (US)

(73) Assignee: The Procter & Gamble Company, Cincinnati, OH (US)

( * ) Notice: Subject to any disclaimer, the term of this patent is extended or adjusted under 35 U.S.C. 154(b) by 162 days.

This patent is subject to a terminal disclaimer.

(21) Appl. No.: 13/749,980

(22) Filed: Jan. 25, 2013

(65) Prior Publication Data

US 2014/0209700 A1 Jul. 31, 2014

(51) Int. Cl.
*A61L 9/12* (2006.01)
*A01M 29/12* (2011.01)

(52) U.S. Cl.
CPC . *A61L 9/12* (2013.01); *A01M 29/12* (2013.01); *A61L 2209/131* (2013.01)

(58) Field of Classification Search
CPC ............... A01M 1/2055; A01M 29/12; A61L 2209/131; A61L 9/12
USPC ......... 239/309, 34–60; 428/35.4, 36.6, 319.3, 428/319.7, 483, 515–520
See application file for complete search history.

(56) References Cited

U.S. PATENT DOCUMENTS 3,702,677 A * 11/1972 Heffington ...................... 239/55
4,157,787 A *  6/1979 Schwartz ......................... 239/56

(Continued)

FOREIGN PATENT DOCUMENTS

WO   WO 03022691 A2 *  3/2003
WO   WO 03077963 A1 *  9/2003

OTHER PUBLICATIONS

Maier, C. Calafut, T. (1998). Polypropylene—The Definitive User's Guide and Databook. William Andrew Publishing/Plastics Design Library. Online version available at: http://app.knovel.com/hotlink/toc/id:kpPTDUGD02/polypropylene-definitive/polypropylene.*

(Continued)

*Primary Examiner* — Len Tran
*Assistant Examiner* — Cody Lieuwen
(74) *Attorney, Agent, or Firm* — Abbey A. Lopez; Amy I. Ahn-Roll

(57) ABSTRACT

A device for delivering a volatile fluid in a continuous manner, over a period of time and without leakage, is disclosed. The device includes a flexible sheet and a semi-rigid sheet that are sealed along their edges to form a closed pocket or reservoir for containing a volatile fluid. The semi-rigid sheet is sealed on a first side to a flexible sheet and sealed on a second side to a vapor permeable membrane. The semi-rigid sheet contains a volatile fluid in the reservoir during storage, preventing contact of the volatile fluid with the vapor permeable membrane before the device is activated. The semi-rigid sheet has a differential score to guide the bounds of an opening that is formed upon activation. Once activated, the vapor permeable membrane provides continuous emission of a volatile fluid from the device.

20 Claims, 2 Drawing Sheets

(56) References Cited

U.S. PATENT DOCUMENTS

| | | | |
|---|---|---|---|
| 4,161,283 A * | 7/1979 | Hyman | 239/55 |
| 4,798,288 A | 1/1989 | Holzner | |
| 4,874,129 A * | 10/1989 | DiSapio et al. | 239/36 |
| 4,998,671 A | 3/1991 | Leifheit | |
| 5,518,790 A * | 5/1996 | Huber et al. | 428/35.2 |
| 5,782,409 A * | 7/1998 | Paul | 239/56 |
| 5,885,701 A * | 3/1999 | Berman et al. | 428/212 |
| 5,961,043 A * | 10/1999 | Samuelson et al. | 239/54 |
| 6,358,577 B1 * | 3/2002 | Bowen et al. | 428/35.3 |
| 7,213,770 B2 | 5/2007 | Martens, III et al. | |
| 7,506,762 B2 | 3/2009 | Nelson et al. | |
| 8,069,985 B2 * | 12/2011 | Burattini | 206/469 |
| 8,709,337 B2 | 4/2014 | Gruenbacher et al. | |
| 2003/0004089 A1 | 1/2003 | Huber et al. | |
| 2008/0190789 A1 | 8/2008 | D'Amico et al. | |
| 2009/0074502 A1 * | 3/2009 | Maloney et al. | 401/133 |
| 2010/0065582 A1 | 3/2010 | Nelson et al. | |
| 2010/0239796 A1 * | 9/2010 | Gagne et al. | 428/34.3 |
| 2010/0308130 A1 * | 12/2010 | Gruenbacher et al. | 239/34 |
| 2011/0167570 A1 * | 7/2011 | Littig | B65D 75/366 8/137 |
| 2011/0180621 A1 | 7/2011 | Gruenbacher et al. | |
| 2014/0048614 A1 | 2/2014 | Santini et al. | |
| 2014/0209698 A1 | 7/2014 | Olchovy et al. | |

OTHER PUBLICATIONS

Search Report for International application No. PCT/US2014/011566, dated Apr. 1, 2014, containing 9 pages.

Search Report for International application No. PCT/US2014/012883, dated Aug. 7, 2014, containing 10 pages.

* cited by examiner

DEVICE FOR DELIVERING A VOLATILE FLUID TO THE ATMOSPHERE

FIELD OF THE INVENTION

The present invention relates to a device for delivering a volatile fluid to the atmosphere in a continuous manner. More specifically, the present invention relates to a low-cost, single-use, portable device having a vapor permeable membrane for continuously delivering, over a period time and without leakage, a volatile fluid to the atmosphere.

BACKGROUND OF THE INVENTION

It is generally known to use a device to evaporate a volatile fluid into a space to deliver a variety of benefits, such as air freshening or reducing malodors. Non-energized systems, for example, systems that are not powered by electrical energy, are a popular way for the delivery of volatile fluids to the atmosphere.

US 2010/0308126A1 to The Procter & Gamble Company offers a delivery engine having a reservoir, a rupturable substrate, vapor permeable membrane sealed to the reservoir, and a rupture tab positioned between the rupturable substrate and the vapor permeable membrane. To breach the rupturable substrate and activate the delivery engine, the rupture tab is compressed perpendicularly to the plane of the rupturable substrate by a user's hand or by insertion of the delivery engine into a housing. Such configuration of the rupture tab may add bulk to the delivery engine, add production/shipping costs, and require additional protective packaging to prevent premature rupture. Additionally, where a thermoformed reservoir is used, a horizontal indexing operation involving thermoforming, filling, and sealing is required to avoid fluid spills from the thermoform during production. This may result in limited throughput processing.

U.S. Pat. No. 8,069,985 to Diapack Ltd. offers a sealed, single-dose, break-open package for containing a product, such as shampoo. The package includes a semi-rigid plastic material and a flexible plastic sheet that is sealed to the semi-rigid plastic material along their perimeters, forming a pocket for containing a dose of product. The semi-rigid plastic material has an incision that varies in depth to guide controlled breakage and form an outlet from which the contents exit the package. A potential issue in using this type of break-open package for continuously delivering a volatile fluid over a period of time is adding a vapor permeable membrane that forms a leak-proof seal between the vapor permeable membrane and the semi-rigid plastic material, at least while the volatile fluid is being emitted to a space. Another potential issue is designing an incision on the semi-rigid plastic material that prevents a volatile fluid from leaking through the incision prior to activation, and prevents the incision from breaking into a sealed edge (i.e. edge where the barrier layer is sealed to the reservoir) and leaking after the device is activated As such, there exists a need for a low cost, single-use, portable device having a vapor permeable membrane for continuously delivering, over a period time and without leakage, a volatile fluid to the atmosphere.

SUMMARY OF THE INVENTION

According to one embodiment of the invention, there is provided a device for delivering a volatile fluid, wherein said device comprises an x-axis, a y-axis, a z-axis, and a sealed edge, wherein said device further comprises a flexible sheet; a multi layer semi-rigid sheet sealed to said flexible sheet to form a reservoir, wherein said semi-rigid sheet comprises a structural layer, a differential score defining a scored region and an un-scored region, wherein said differential score comprises at least one incision having a depth along said z-axis that transverses at least about 50% of said structural layer, and wherein said un-scored region is about 5 mm to about 15 mm from said sealed edge; and a vapor permeable membrane sealed to said semi-rigid sheet.

According to another embodiment of the invention, there is provided a device for delivering a volatile fluid wherein said device comprises an x-axis, a y-axis, a z-axis, and wherein said device further comprises a reservoir for containing a volatile fluid. The device also comprises a multi layer semi-rigid sheet comprising a first sealant layer sealed to said reservoir; a barrier layer sealed to said first sealant layer; a structural layer sealed to said barrier layer; optionally, a second sealant layer sealed to said structural layer; wherein said multi layer semi-rigid sheet further comprises a differential score comprising an upper incision and a lower incision, said upper incision has a depth along said z-axis that transverses at least about 50% of said structural layer and said lower incision transverses at least about 50% of said first sealant layer. The device also comprises a vapor permeable membrane heat-sealed to said semi-rigid sheet.

According to yet another embodiment of the invention, there is provided a device for delivering a volatile fluid wherein said device comprises an x-axis, a y-axis, a z-axis, and a sealed edge, and wherein said device further comprises a flexible sheet. The device also comprises a multi layer semi-rigid sheet sealed to said flexible sheet to form a reservoir for containing a perfume mixture. The multi layer semi-rigid sheet comprises a first sealant layer heat-sealed to said flexible sheet, wherein said first sealant layer comprises a material selected from the group consisting of polyethylene, polypropylene, polyethylene terpthalate, and combinations thereof, and wherein said first sealant layer has a thickness along said z-axis of at least about 15 microns; a perfume resistant barrier layer sealed to said first sealant layer, wherein said barrier layer comprises a material selected from the group consisting of polyethylene, ethylene vinyl alcohol, and combinations thereof, and wherein said barrier layer comprises a thickness along said z-axis from about 10 microns to about 15 microns; a structural layer sealed to said perfume resistant barrier layer, wherein said structural layer comprises a plastic selected from the group consisting of polystyrene, polyvinyl chloride, acrylonitrile butadiene styrene, polypropylene, polyethylene, polyethylene terpthalate, and combinations thereof, and wherein said barrier layer comprises a thickness along said z-axis of about 350 microns; a differential score defining a scored region and an un-scored region, wherein said differential score comprises at least one incision having a depth along said z-axis that transverses at least about 50% of said structural layer, and wherein said un-scored region is about 5 mm to about 15 mm from said sealed edge; and, optionally, a second sealant layer heat-sealed to said structural layer and consisting of polyethylene, polypropylene, polyethylene terpthalate, and combinations, wherein said second sealant layer comprises a thickness along said z-axis of at least about 15 ums, and wherein said differential score fully transverses said second sealant layer. The device also comprises a microporous membrane heat-sealed to said semi-rigid sheet.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

DETAILED DESCRIPTION OF THE INVENTION

The device comprises, consists essentially of, or consists of, various combinations of the materials, features, structures, and/or characteristics described herein.

The device of the present invention is suitable for purposes of providing fragrances, air fresheners, deodorizers, odor eliminators, malodor counteractants, insecticides, insect repellants, medicinal substances, disinfectants, sanitizers, mood enhancers, and aromatherapy aids, or for any other purpose using a volatile fluid that acts to condition, modify, or otherwise change the atmosphere or the environment.

Figure 1:
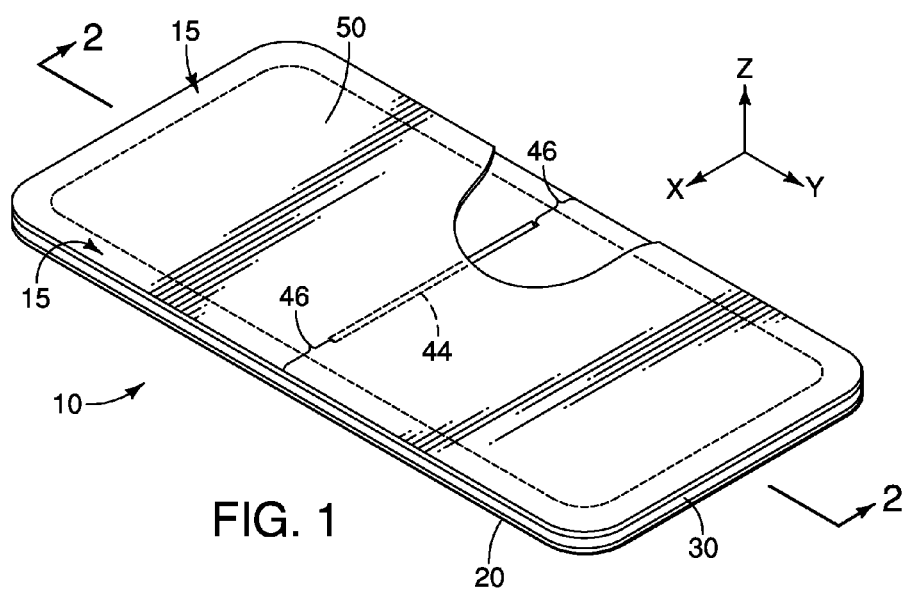
FIG. 1 shows a cut-away perspective view of an embodiment of a device according to the present invention.
Figure 2:
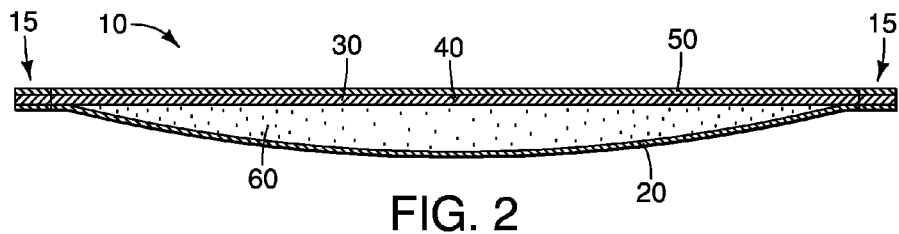
FIG. 2 shows a cross-sectional view, taken along lines 2-2 of the device in FIG. 1.

Referring to FIGS. 1 and 2, a device 10 in accordance with one embodiment of the present invention is shown. The device 10 includes a flexible sheet 20, a semi-rigid sheet 30 having a score 40, and a vapor permeable membrane 50. The semi-rigid sheet 30 has a first side 33 that is sealed to the flexible sheet 20 along the device's periphery, forming a closed pouch or reservoir 60. This sealed periphery of the device 10 is referred to herein as the "edge" 15 and may be about 5 mm in width. While one reservoir 60 is shown in FIG. 2, a plurality of reservoirs, formed by sealing off a plurality of pouches with the flexible sheet 20 and semi-rigid sheet 30, may also be provided. The semi-rigid sheet 30 is sealed along the edge 15 on a second side 39 to a vapor permeable membrane 50. The semi-rigid sheet 30 contains a volatile fluid in the reservoir 60, preventing contact of the volatile fluid with the vapor permeable membrane 50 before the device 10 is activated. The semi-rigid sheet 30 has a differential score 40 to guide the boundary of an opening that is formed upon activation of the device 10. Once activated, the vapor permeable membrane 50 provides continuous emission of a volatile fluid from the device 10. The continuous emission of a volatile fluid can be of any suitable length, including but not limited to, up to: 20 days, 30 days, 60 days, 90 days, 120 day or any period between 30 to 120 days, without leakage.

The term "volatile fluid" as used herein, refers to a material that is vaporizable at room temperature and atmospheric pressure without the need of an energy source. The volatile fluid may be a composition comprised entirely of a single volatile fluid. The volatile fluid may also be a composition comprised entirely of a volatile fluid mixture (i.e. the mixture has more than one volatile component). Further, it is not necessary for all of the component materials of the composition to be volatile. Any suitable volatile fluid in any amount or form, including a liquid or emulsion, may be used.

Volatile fluid suitable for use herein may, thus, also have non-volatile components, such as carrier materials (e.g., water, solvents, etc). It should also be understood that when the volatile fluid is described herein as being "delivered" or "emitted", this refers to the volatilization of the volatile component thereof, and does not require that the non-volatile components thereof be emitted.

The device 10 may be compact and easily portable (e.g. sized to fit in a clothing pocket, wallet, purse, etc.). Although FIGS. 1-4 show a stand-alone device, it is contemplated that the device 10 may be used with known diffusion assistance means, such as heaters and fans, to deliver volatile fluids to the atmosphere.

The device 10 includes a width, length, and depth along an x-axis, y-axis, and z-axis, respectively. The device 10 may be elongate in that its length to width ratio is about 2:1 to about 4:1, alternatively about 1.5:1 to about 2.5:1. The device 10 may have a length of about 45 mm to about 55 mm, alternatively about 51 mm; a width of about 15 mm to about 30 mm to about, alternatively about 23 mm; a depth of about 5 mm to about 15 mm, alternatively about 11 mm. The dimensions of the reservoir 60 may be such that it holds about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of volatile fluid.

Flexible Sheet

The device 10 includes a flexible sheet 20 that is sealable to the semi-rigid sheet 30 and is a significant barrier to both liquid and vaporous volatile material. Having a flexible pouch type reservoir enables production of the device 10 on a high throughput, more cost-effective vertical form, fill, and seal process.

The flexible sheet 20 is made of a material that provides sufficient flexibility to bend with the semi-rigid sheet 30 and breach the differential score 40 in the semi-rigid sheet 30. Flexible sheet materials are known in the art, and may comprise polyethylene ("PE"), polyethylene terpthalate ("PET"), metallized PET, aluminum ("ALU"), oriented polypropylene ("OPP"), oriented polyamide ("OPA"), polyacrylonitrile (e.g. Barex™), ethylene vinyl alcohol ("EVOH"), and combinations or laminates thereof.

Table 1 shows the possible material blends and thickness combinations of the flexible sheet.

TABLE 1

| Type of laminate | Thickness (microns) |
| --- | --- |
| PET/PE | PET 12-30/PE 20-150 |
| PET/EVOH/PE | PET 12-30/EVOH 15-20/PE 30-150 |
| PET/ALU/PE | PET 12-30/ALU 6-30/PE 20-150 |
| OPP/ALU/PE | OPP 15-30/ALU 6-30/PE 20-150 |
| OPA/ALU/PE | OPA 15-30/ALU 6-30/PE 20-150 |

Semi-Rigid Sheet

Figure 3:
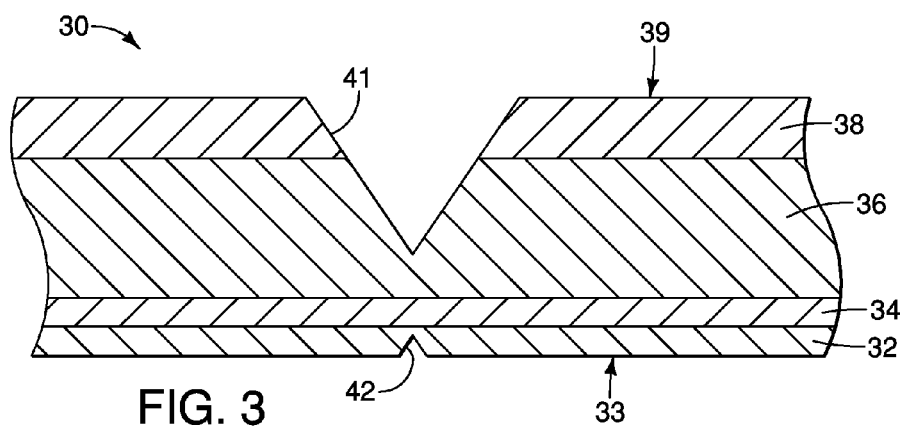
FIG. 3 shows an enlarged portion of the semi-rigid sheet 30 and the score 40, shown in FIG. 2.

The device 10 also includes a multi-layer semi-rigid sheet 30 that is heat-sealable on both sides. Referring to FIG. 3, the semi-rigid sheet 30 comprises a first sealant layer 32 having a first side 33 that is heat-sealable to the flexible sheet 20, a barrier layer 34, a structural layer 36, and a second sealant layer 38 having a second side 39 that is heat-sealable to a vapor permeable membrane 50. Perfume resistant tie layers may be included between each layer of the semi-rigid sheet 30. Each tie layer comprises water-based or organic solvent-based polyurethane, polyurea, ethylene acrylic acid, PE, polypropylene ("PP"), maleic anhydride, or other organic chemical resistant compounds. In some embodiments, the tie layer comprises polyurethane.

First sealant layer 32 is heat-sealable to the flexible sheet 20. First sealant layer 32 may be made of any material that is heat-sealable to its adjacent layer. In the embodiment shown in FIG. 3, the adjacent layer is the flexible sheet 20. First sealant layer 32 may comprises PE, PP, PET, or combinations thereof. Adjacent layer (e.g. flexible sheet 20) may be made of the same material as the first sealant layer 32. For example, where the first sealant layer 32 is PE, the flexible sheet 20 is also made of PE. First sealant layer 32 has a thickness along the z-axis ranging from about 15 microns to about 300 microns, alternatively from about 15 microns to about 200 microns, alternatively from about 15 microns to about 100 microns, alternatively from about 15 microns to about 50 microns, alternatively about 35 microns, alternatively about 20 microns.

The barrier layer 34 can be made of any material that ruptures with applied force, with or without the presence of an element to aid in such rupture. Because the barrier layer 34 is intended to contain a volatile fluid while in storage, it may be made from a material which is chemically resistant to volatile fluids, including perfumes and solvents, and prevents evaporation of the volatile fluid prior to its intended use. Such materials may be impermeable to vapors and liquids. Suitable materials for the barrier layer 34 include a flexible film, such as a polymeric film, a flexible aluminum or metal foil, or a composite material such as foil/polymeric film laminate. Suitable flexible foils include a 20 micron aluminum foil. Suitable polymeric films include PET films, acrylonitrile copolymer barrier films such as those sold under the tradename Barex® by INOES, chlorotrifluoroethylene (e.g. Aclar™), EVOH, and combinations thereof. It is also contemplated that coated barrier films may be utilized as a barrier layer. Such coated barrier films include metalized PET, metalized PP, silica or alumina coated film may be used. Any barrier material, whether coated or uncoated, may be used alone and or in combination with other barrier materials.

Barrier layer 34 has a thickness that is sufficient to serve as a perfume barrier during normal storage times yet thin enough to break open when the device 10 is activated. Suitable thicknesses in the z-direction include about 5 microns to about 30 microns, alternatively about 5 microns to about 15 microns. The thickness of the barrier layer will vary depending on the material of choice. Where aluminum foil is used, for example, the thickness may be about 20 to about 25 microns.

In some embodiments, the semi-rigid sheet 30 may include a second or supplemental barrier layer (not shown) akin to barrier layer 34. In such case, the supplemental barrier layer may be heat-sealable to the first side 33 and the flexible sheet 20 to provide supplemental protection and help prevent fluid in the reservoir 60 from passing through the differential score 40 while in storage.

Structural layer 36 may comprise one of the following materials: polystyrene (PS), polyvinyl chloride ("PVC"), acrylonitrile butadiene styrene ("ABS"), PET, PE, PP, nylon, nylon composites, or combinations thereof. In one embodiment, the structural layer is made of PET or PP or combinations thereof. Structural layer 36 may have a thickness along the z-axis that ranges from about 200 microns to about 750 microns, alternatively from about 300 microns to about 750 microns, alternatively from about 350 microns to about 700 microns, alternatively from about 300 microns to about 450 microns, alternatively from about 300 microns to about 400 microns, alternatively from about 300 microns to about 350 microns.

Table 2 shows suitable material blends and thickness combinations of the structural layer 36.

TABLE 2

| Type of laminate | Thickness (microns) |
|---|---|
| PS/PE | PS 300-700/PE 20-50 |
| PS/PP | PS 300-700/PP 20-50 |
| PVC/PE | PVC 300-700/PE 20-50 |
| ABS/PE | ABS 300-700/PE 20-50 |
| PP/PE | PP 300-700/PE 20-50 |

The semi-rigid sheet 30 also includes a second sealant layer 38 having a second side 39 that is heat-sealable to the vapor permeable membrane 50. Second sealant layer 38 may be made from PE, PP, or combinations thereof. Suitable thicknesses for the second sealant layer 38, along the z-axis, range from about 15 microns to about 300 microns, alternatively from about 15 microns to about 200 microns, alternatively from about 15 microns to about 100 microns, alternatively from about 15 microns to about 50 microns, alternatively from about 20 microns to about 50 microns, alternatively from about 35 microns, alternatively about 20 microns.

In some embodiments, the semi-rigid sheet 30 comprises a first sealant layer 32 of about 35 micron thick PE, a barrier layer 34 of about 10 micron thick EVOH, a structural layer 36 of about 450 micron thick PS, and a second sealant layer 38 of about 35 micron thick PE. Thus, the semi-rigid sheet may have a total thickness of about 530 microns, a typical weight of about 500 g/m2, a typical break load of about 16 N/mm2, and a typical modulus of elasticity of about 1500 to about 3500, alternatively about 2200 N/mm2. In other embodiments, the semi-rigid sheet 30 comprises a combined second sealant layer and structural layer of about 200 micron PP, 10 micron EVOH barrier layer, and a 200 micron PP first sealant layer. In other embodiments, the semi-rigid sheet 30 comprises 50 micron PE second sealant layer, 350 micron PET structural layer, 20 micron PE/10 micron EVOH barrier layer, and 20 micron PE first sealant layer.

The semi-rigid sheet 30 includes at least one differential score 40 on the x-y plane. "Differential score" means a score having an incision depth that varies along the length of the incision along the x-axis (or y-axis in some embodiments) of the semi-rigid sheet 30. The differential score 40 may run along the x-axis or, in some embodiments, along the y-axis. The differential score 40 does not run the across the entire length of the x-axis (i.e. width of the device 10). Rather, the differential score 40 is positioned between the edge 15 so that the differential score 40 terminates prior to meeting the sealed edge 15 of the device (i.e. where the semi-rigid sheet 30 is sealed to the flexible sheet 20 and the vapor permeable membrane 50). The region(s) of the semi-rigid sheet 30 having a differential score 40 is considered the scored region(s) 44. The regions of the semi-rigid sheet 30 extending from the ends of the differential score 40 (i.e. along the same axis as a differential score or in-line with the differential score) are considered the un-scored regions 46.

The device 10 may comprises more than one differential score arranged in any format on the x-y plane to facilitate breaching the structural layer 36, yet not breaching the sealed edge 15. In some embodiments, the device 10 may include two intersecting differential scores (i.e. two incisions that intersect one another along the x-y plane. Further, the device 10 may include such intersecting differential score pattern on the first side 33 and second side 39 of the semi rigid sheet 30.

The un-scored regions 46 of the semi-rigid sheet 30 are from about 5 mm to about 15 mm, alternatively from about 5 mm to about 10 mm, alternatively about 5 mm from the sealed edge 15. The material of the semi-rigid sheet 30 may affect the distance of the differential score along the x-axis (e.g.

higher modulus may require greater amount of un-scored region). Creating a differential score 40 that is too close to the edge 15 may risk breaking the sealed edge 15, resulting in leakage of the fluid. Creating a differential score 40 that is greater than 15 mm from the edge 15 may prevent sufficient quantities of volatile fluid from contacting the vapor permeable membrane 50, limiting delivery of volatile fluids to the atmosphere.

The cross-sectional form of the differential score 40 may take on various shapes. It may be curved (e.g. in the form of an arc of a circle or an arc of an ellipse), or may be V-shaped as shown in FIG. 3, U-shaped, L-shaped, or combinations thereof. In some embodiments, differential score 40 may be inclined (i.e. may slope with respect to the sides of the semi-rigid sheet 30).

Differential score 40 may comprise a single upper incision 41 or an upper incision 41 and a lower incision 42. The upper and lower incisions do not transverse the barrier layer 34. More specifically, the upper and lower incisions are deepest along a central portion of the differential score 40. In other words, breakage along differential score 40 is always gradual (i.e. proportional to the extent to which device 10 is bent), so that, when device 10 is bent relatively lightly, the semi-rigid sheet 30 only breaks along the central portion of the differential score 40. And, as device 10 is bent further, breakage of the semi-rigid sheet 30 also extends to the peripheral portions of the differential score 40.

The depth of the upper incision 41, along the z-axis as shown in FIG. 3, transverses the thickness of the second sealant layer 38 and from about 40% to about 100%, alternatively from about 50% to about 100%, alternatively from about 50% to about 90%, alternatively from about 60% to about 100%, alternatively from about 70% to about 100%, alternatively at least about 50% of the depth of the structural layer 36. The depth of the lower incision 42, in the z-direction, transverses a portion or traverses the entire first sealant layer 32. The depth of the lower incision 42 transverses from about 50% to about 100%, alternatively from about 50% to about 90%, alternatively about 65%, alternatively about 80% of the depth of the first sealant layer 32.

Where a semi-rigid sheet comprises 50 micron PE/350 micron PET/20 micron PE/10 micron EVOH/20 micron PE, the maximum depth of the upper incision 41 may be 420 microns through the PE/PET/PE layers and the maximum depth of the lower incision 42 may be 20 microns through the last PE layer. Where a semi-rigid sheet comprises 200 micron PP/10 micron EVOH/200 micron PP, the maximum depth of the differential score 40 may be 200 microns for either upper or lower incision; the other incision having a maximum depth of less than 200 microns.

Vapor Permeable Membrane

A vapor permeable membrane 50 is sealed to the edge 15 of the second side 39 of the second sealant layer 38 such that the vapor permeable membrane 50 is on the outside of the device 10 and exposed to the atmosphere. A vapor permeable membrane will prevent volatile fluid from leaking from the device 10 while allowing volatile vapor to exit the device 10. The vapor permeable membrane 50 is sufficiently flexible to withstand flexion of the device 10 when the semi-rigid sheet 30 is being breached. The vapor permeable membrane 50 also prevents free flow of fluid out of the vapor permeable membrane 50, thus addressing leakage problems.

While not wishing to be bound by theory, the physical characteristics of a membrane may affect the diffusion or transfer rate of volatile fluids through the vapor permeable membrane 50. Such characteristics may include materials used, use of fillers, pore size, thickness, and evaporative surface area. Suitable vapor permeable membranes for the present invention include an ultra high molecular weight polyethylene (UHMWPE) type membrane optionally filled with silica as described in US 2010/0308126A1. Such UHMWPE membranes include Daramic™ V5, available from Daramic; Solupor®, available from DSM (Netherlands); Teslin™ SP1100HD, available from PPG Industries; and combinations thereof. It is believed that these membranes flex and allow a volatile fluid to freely dissipate while containing fluid within the device 10. Other vapor permeable membranes include traditional PE, PP, ethylene vinyl acetate, and combinations thereof.

In one aspect of the invention, the vapor permeable membrane 50 may include a dye that is sensitive to the amount of volatile fluid it is in contact with to indicate end-of-life. Alternatively, the membrane 50 may change to transparent when in contact with a fragrance or volatile fluid to indicate diffusion is occurring. Other means for indicating end-of-life that are known in the art are contemplated for the present invention.

The vapor permeable membrane 50 may have a thickness along the z-axis, of about 0.01 mm to about 1 mm, alternatively from about 0.1 mm to 0.4 mm, alternatively from about 0.15 mm to about 0.35 mm, alternatively about 0.25 mm.

Those of ordinary skill in the art will appreciate that the surface area of the membrane 50 can vary depending on the user preferred size of the device 10. In some portable embodiments, the evaporative surface area of the membrane may be about 2 $cm^2$ to about 100 $cm^2$, alternatively about 2 $cm^2$ to about 35 $cm^2$, alternatively about 10 $cm^2$ to about 50 $cm^2$, alternatively about 10 $cm^2$ to about 45 $cm^2$, alternatively about 10 $cm^2$ to about 35 $cm^2$, alternatively about 15 $cm^2$ to about 40 $cm^2$, alternatively about 15 $cm^2$ to about 35 $cm^2$, alternatively about 20 $cm^2$ to about 35 $cm^2$, alternatively about 30 $cm^2$ to about 35 $cm^2$, alternatively about 35 $cm^2$ to 40 $cm^2$.

The vapor permeable membrane 50 may be secured to the second side 39 of the second sealant layer 38 along the edge 15 by a layer of adhesives, heat and/or pressure sealing, ultrasonic bonding, crimping, and the like or a combination thereof. Once breached, the volatile fluid flows out of the reservoir 60, through the semi-rigid sheet 30, contacting the vapor permeable membrane 50, and is then delivered to the atmosphere. Because the vapor permeable membrane 50 is shielded from the volatile fluid until the semi-rigid sheet 30 is breached, the fragrance intensity may build slowly from zero to its equilibrium rate of release when the vapor permeable membrane 50 is fully wetted.

Depending on the final configuration of the device 10, additional parts may be added. Such parts may serve the purpose of, for example, providing intensity control or protection from contamination, dust, and the like during shipment.

Figure 4:
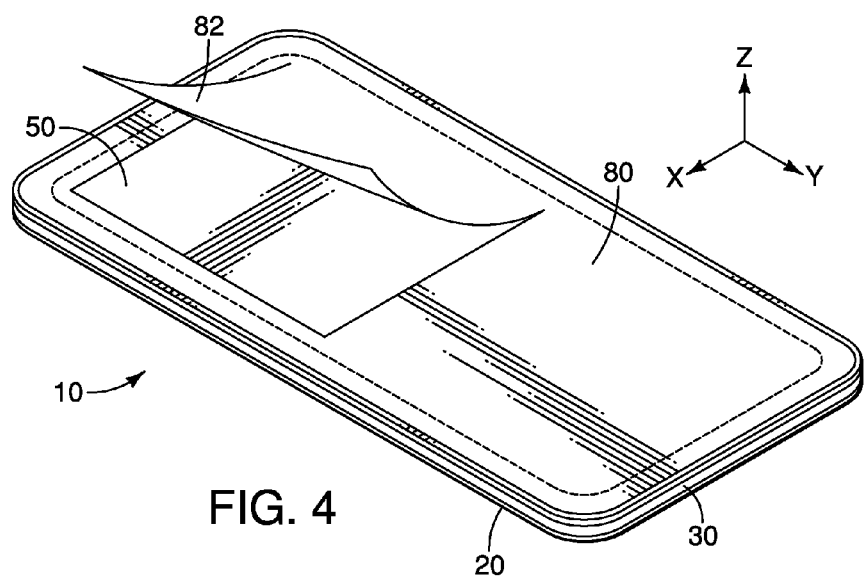
FIG. 4 shows an embodiment of the device, according to the present invention, with an intensity control sheet.

Referring to FIG. 4, the device 10 may include an intensity control sheet 80. The intensity control sheet 80 may be made of any material that slows diffusion of a volatile composition from the device 10. The intensity control sheet 80 may also be made from a printable material available in the art to print user instructions, decorative artwork, or the like. The intensity control sheet 80 may be heat-sealed, crimped, bonded or otherwise attached to the vapor permeable membrane 50. In the embodiment shown in FIG. 4, the intensity control sheet 80 includes a single opening to reveal the vapor permeable membrane 50 and includes a cover 82. The cover 82 can be opened or closed in varying degrees by a user to control the intensity of the volatile fluid from the reservoir 60 to the atmosphere.

In other embodiments, the intensity control sheet 80 may have adjustable vents or apertures. For example, the intensity control sheet 80 may comprises a vented layer having one or more vents and an unvented layer positioned over the vents. The vented or the unvented layer may slide or pivot to reveal the vents and allow intensity control of the volatile fluid from the reservoir 60 to the atmosphere. Increasing the size of the vents, may increase the delivery of volatile fluid. Opening of the vents can be controlled by the user through a variety of means. A user may open, partially open, partially close, or close the vents.

Figure 5A:
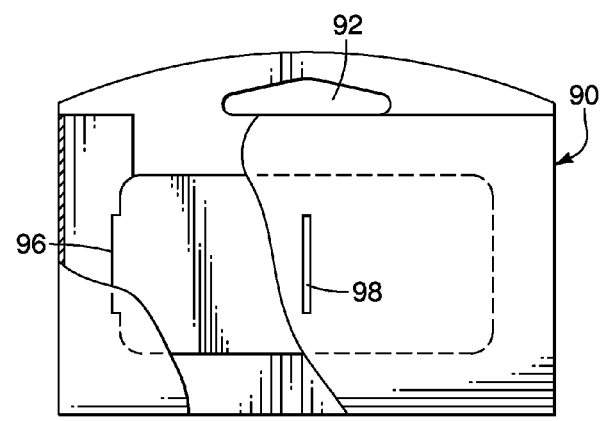
FIG. 5A shows a cut-away rear elevational view of a device, according to the present invention, surrounded by a housing.
Figure 5B:
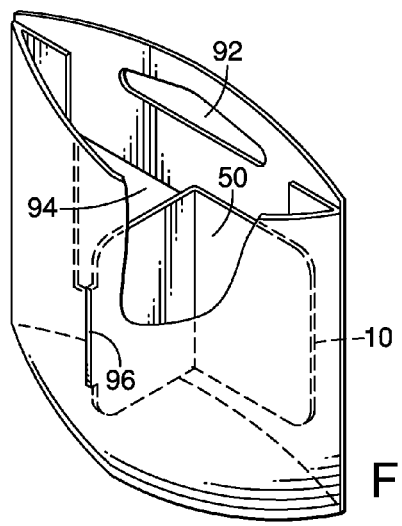
FIG. 5B shows a cut-away rear perspective view of the device and housing in FIG. 5A in an activated, upright configuration.

Referring to FIGS. 5A and 5B, the device 10 may also include a housing 90 that serves as an intensity control feature and as an upright stand for the device 10. The housing 90 can also serve as the outer packaging of the device 10 for transport and display in a retail location. The housing 90 may be made from any commercially available material including paper, cardboards and plastics.

The housing 90 may be made from a single panel that circumferences the device 10 and is secured on one side as shown in FIGS. 5A and 5B. The housing 90 may also formed with multiple panels secured together with an adhesive or the like in any configuration to surround, at least in part, the device 10. During transport and/or prior to activation of the device, the housing may be in a flat configuration as shown in FIG. 5A. The housing may include an opening 92 for hanging from a display hook at a retail location. The housing 90 may define a window 94 that shows the device to the user. The window 94 may comprise a transparent sheet revealing the flexible sheet 30 or the window 94 may be an unobstructed opening in the housing 90. In some embodiments, the housing 90 does not include a window 94.

The device 10 may include a tab 96 extending therefrom. The device 10 is activated and set upright in one step by creating an approximate 90 degree bend in the device to breach the score 40. This can be done by pushing the tab 96 side of the device towards a notch 98 in the housing 10 as shown in FIG. 5B. In FIG. 5B, the approximate 90 degree bend is created on the side of the vapor permeable membrane 50. Once bent, the tab 96 is inserted into the notch 98. In this way, the tab 96 locks into the notch 98 to stand the device 10 in an upright position while facilitating delivery of the volatile fluid to the atmosphere.

Volatile Fluid

The volatile fluid can be in the form of perfume oil. Most conventional fragrance materials are volatile essential oils. The volatile fluid can be a volatile organic compound commonly available from perfumery suppliers. Furthermore, the volatile fluid can be synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. In the case of air freshener or fragrances, the different volatile fluids can be similar, related, complementary, or contrasting.

The volatile fluid may also originate in the form of a crystalline solid, which has the ability to sublime into the vapor phase at ambient temperatures or be used to fragrance a liquid. Any suitable crystalline solid in any suitable amount or form may be used. For example, suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like.

It may not be desirable, however, for volatile fluids to be closely similar if different volatile fluids are being used in an attempt to avoid the problem of emission habituation. Otherwise, the people experiencing the emissions may not notice that a different material is being emitted. The different emissions can be provided using a plurality of delivery systems each providing a different volatile fluid (such as, musk, floral, fruit emissions, etc). The different emissions can be related to each other by a common theme, or in some other manner. An example of emissions that are different, but complementary might be a cinnamon emission and an apple emission.

In addition to the volatile fluid of the present invention, the device 10 may include any known malodor composition to neutralize odors. Suitable malodor compositions include cyclodextrin, reactive aldehydes and ionones.

The composition may be formulated such that the composition comprises a volatile fluid mixture comprising about 10% to about 100%, by total weight, of volatile fluids each having a VP at 25° C. of less than about 0.01 torr; alternatively about 40% to about 100%, by total weight, of volatile fluids each having a VP at 25° C. of less than about 0.1 torr; alternatively about 50% to about 100%, by total weight, of volatile fluids each having a VP at 25° C. of less than about 0.1 torr; alternatively about 90% to about 100%, by total weight, of volatile fluids each having a VP at 25° C. of less than about 0.3 torr. In one embodiment, the volatile fluid mixture may include 0% to about 15%, by total weight, of volatile fluids each having a VP at 25° C. of about 0.004 torr to about 0.035 torr; and 0% to about 25%, by total weight, of volatile fluids each having a VP at 25° C. of about 0.1 torr to about 0.325 torr; and about 65% to about 100%, by total weight, of volatile fluids each having a VP at 25° C. of about 0.035 torr to about 0.1 torr. One source for obtaining the saturation vapor pressure of a volatile fluid is EPI Suite™, version 4.0, available from U.S. Environmental Protection Agency.

The viscosity of a volatile fluid may control how and when a volatile fluid is delivered to the vapor permeable membrane 50. For example, less viscous compositions may flow faster than the more viscous volatile fluids. Thus, the membrane may be first wetted with the less viscous materials. The more viscous volatile fluid, being slightly less or of similar density with the less viscous phase, may remain in the reservoir via gravity. Thus, the less viscous volatile fluid may be delivered to the vapor permeable membrane 50 and emitted to the atmosphere more quickly. To help prevent liquid from seeping through the vapor permeable membrane 40, volatile fluids may have viscosities less than about 23 cP and surface tension less than about 33 mN/m.

In one embodiment, the composition containing a volatile fluid may have a viscosity of about 1.0 cP to less than about 25 cP, alternatively about 1.0 cP to less than about 23, alternatively about 1.0 cP to less than about 15 cP.

The composition containing a volatile fluid may be designed such that the composition may include a surface tension of about 19 mN/m to less than about 33 mN/m, alternatively about 19 mN/m to less than about 30 mN/m, alternatively about 19 mN/m to less than about 27 mN/m.

As used in this specification and the appended claims, the singular forms "a", "an", and "the" include plural references unless the content clearly dictates otherwise. Thus, for example, "a volatile fluid" may include more than one volatile fluid Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A device for delivering a volatile fluid, wherein said device comprises an x-axis, a y-axis, a z-axis, and a sealed edge, wherein said device further comprises:
   a. a flexible sheet;
   b. a multi layer semi-rigid sheet comprising a first reservoir side and a second membrane side, wherein said first reservoir side is sealed to said flexible sheet to form a reservoir, wherein said semi-rigid sheet comprises:
      i. a structural layer,
      ii. a differential score comprising a varied incision depth, wherein said differential score extends along either said x-axis or said y-axis and terminates at endpoints located inside the boundaries of said sealed edge to minimize leakage of said volatile fluid through said sealed edge, wherein said differential score comprises at least one incision having a depth along said z-axis that transverses at least about 50% of said structural layer; and
   c. a vapor permeable membrane comprising a first semi-rigid sheet side and a second atmosphere side wherein said first semi-rigid sheet side is sealed to said second membrane side of said semi-rigid sheet such that the vapor permeable membrane will prevent volatile liquid from leaking from the device while allowing volatile vapor to exit the device.

2. The device of claim 1, further comprising an un-scored region is about 5 mm to about 10 mm from said sealed edge.

3. The device of claim 1, wherein said semi-rigid sheet further comprises a first sealant layer, and wherein said differential score comprises an upper incision and a lower incision, wherein said lower incision has a depth, along said z-axis, that transverses at least 50% of said first sealant layer.

4. The device of claim 1, wherein said semi-rigid sheet further comprises a second sealant layer sealed to said structural layer and to said vapor permeable membrane, wherein said second sealant layer comprises a material selected from the group consisting of polyethylene, polypropylene, and combinations thereof.

5. The device of claim 1, wherein said semi-rigid sheet further comprises a perfume resistant barrier layer sealed to said structural layer and comprising a material selected from the group consisting of: ethylene vinyl alcohol, metal foil, and combinations thereof.

6. The device of claim 1, wherein said semi-rigid sheet comprises at least 3 materials selected from the group consisting of: polyethylene, polyethylene terpthalate, ethylene vinyl alcohol, polypropylene, polystyrene, and combinations thereof.

7. The device of claim 1, wherein said semi-rigid sheet comprises polyethylene, ethylene vinyl alcohol, and polypropylene.

8. The device of claim 1, wherein said structural layer comprises about 200 micron thick polypropylene, and wherein said semi-rigid sheet further comprises a first sealant layer of about 200 micron thick polypropylene, a bather layer of about 10 micron thick ethylene vinyl alcohol, and a second sealant layer of about 35 microns.

9. The device of claim 1, wherein said semi-rigid sheet has a modulus of elasticity of about 2200 N/mm2.

10. The device of claim 1, wherein said device further comprises a volatile fluid mixture contained in said reservoir, wherein said volatile fluid mixture comprises about 90% to about 100%, by total weight, of volatile fluids each having a VP at 25° C. of less than about 0.3 torr.

11. The device of claim 1, wherein said device further comprises a perfume mixture contained in said reservoir.

12. The device of claim 1, wherein said vapor permeable membrane is a microporous membrane comprising an average pore size of about 0.01 to about 0.03 microns.

13. The device of claim 12, wherein said vapor permeable membrane comprises an average pore size of about 0.02 microns.

14. The device of claim 1, wherein the evaporative surface area of said vapor permeable membrane is about 2 cm$^2$ to about 35 cm$^2$.

15. The device claim 1 further comprising an intensity control sheet attached to said vapor permeable membrane.

16. The device of claim 1, wherein said device is contained in a housing.

17. The device of claim 16, wherein said housing comprises a notch, and wherein said device further comprises a tab extending from said device, said tab is configured to insert into said notch.

18. A device for delivering a volatile fluid, wherein said device comprises an x-axis, a y-axis, a z-axis, and wherein said device further comprises:
   a. a reservoir for containing a volatile fluid;
   b. a multi layer semi-rigid sheet comprising:
      i. a first sealant layer sealed to a flexible sheet to form a reservoir,
      ii. a barrier layer sealed to said first sealant layer,
      iii. a structural layer sealed to said barrier layer,
      iv. a second sealant layer sealed to said structural layer,
      wherein said multi layer semi-rigid sheet further comprises a differential score comprising an upper incision and a lower incision, said upper incision has a depth along said z-axis that transverses at least about 50% of said structural layer and said lower incision has a depth along said z-axis that transverses at least about 50% of said first sealant layer; and
   c. a vapor permeable membrane heat-sealed to the outermost periphery on one side of said second sealant layer of said semi-rigid sheet such that the vapor permeable membrane will prevent volatile liquid from leaking from the device while allowing volatile vapor to exit the device.

19. The device of claim 18, wherein said upper incision transverses the thickness of second sealant layer and from about 50% to about 90% of the thickness of said structural layer, and wherein said lower incision transverses from about 50% to about 90% of said first sealant layer.

20. A device for delivering a volatile fluid, wherein said device comprises an x-axis, a y-axis, a z-axis, and a sealed edge, and wherein said device further comprises:
   a. a flexible sheet;
   b. a multi layer semi-rigid sheet comprising a first reservoir side and a second membrane side, wherein said first reservoir side is sealed to said flexible sheet to form a reservoir for containing a perfume mixture, wherein said semi-rigid sheet comprises:
      i. a first sealant layer heat-sealed to said flexible sheet, wherein said first sealant layer comprises a material selected from the group consisting of polyethylene, poylpropylene, polyethylene terpthalate, and combinations thereof, and wherein said first sealant layer has a thickness along said z-axis of at least about 15 microns,
      ii. a perfume resistant barrier layer sealed to said first sealant layer, wherein said barrier layer comprises a material selected from the group consisting of polyethylene, ethylene vinyl alcohol, and combinations thereof, and wherein said perfume resistant barrier layer comprises a thickness along said z-axis from about 10 microns to about 15 microns;
      iii. a structural layer sealed to said perfume resistant barrier layer, wherein said structural layer comprises a plastic selected from the group consisting of polystyrene, polyvinyl chloride, acrylonitrile butadiene styrene, polypropylene, polyethylene, polyethylene terpthalate, and combinations thereof, and wherein said structural layer comprises a thickness along said z-axis from about 350 microns to about 700 microns;
      iv. a differential score comprising a varied incision depth, wherein said differential score extends along said either said x-axis or said y-axis and terminates at endpoints located inside the boundaries of said sealed edge to minimize leakage of said volatile fluid through said sealed edge, wherein said differential score comprises at least one incision having a depth along said z-axis that transverses at least about 50% of said structural layer; and
      v. optionally, a second sealant layer heat-sealed to said structural layer comprising a material selected from the group consisting of polyethylene, polypropylene, polyethylene terpthalate, and combinations, and wherein, when said second sealant layer is present, said second sealant layer comprises a thickness along said z-axis of at least about 15 microns, and wherein said differential score fully transverses said second sealant layer; and
   c. a microporous membrane comprising a first semi-rigid sheet side and a second atmosphere side wherein said first semi-rigid sheet side is heat-sealed to said second membrane side of said semi-rigid sheet such that the vapor permeable membrane will prevent volatile liquid from leaking from the device while allowing volatile vapor to exit the device.

\* \* \* \* \*